United States Patent
Piccinini et al.

(10) Patent No.: US 9,765,292 B2
(45) Date of Patent: Sep. 19, 2017

(54) BIOREACTOR AND RACK FOR MOUNTING BIOREACTORS

(71) Applicants: CELLEC BIOTEK AG, Basel (CH); UNIVERSITY HOSPITAL OF BASEL, Basel (CH)

(72) Inventors: Elia Piccinini, Toronto (CA); David Wendt, Arlesheim (CH); Adam Papadimitropoulos, Basel (CH); Laura Spinelli, Lainate (IT); Stefania Adele Riboldi, Biassono (IT); Francesco Giovanni Greco, Cantù (IT); Peter Iwatschenko, Eckental (DE)

(73) Assignees: University Hospital of Basel, Basel (CH); Cellec Biotek AG, Basel (CH)

( * ) Notice: Subject to any disclaimer, the term of this patent is extended or adjusted under 35 U.S.C. 154(b) by 0 days.

(21) Appl. No.: 14/406,043

(22) PCT Filed: Jun. 4, 2013

(86) PCT No.: PCT/EP2013/061514
§ 371 (c)(1),
(2) Date: Dec. 5, 2014

(87) PCT Pub. No.: WO2013/182574
PCT Pub. Date: Dec. 12, 2013

(65) Prior Publication Data
US 2015/0197719 A1     Jul. 16, 2015

(30) Foreign Application Priority Data

Jun. 6, 2012 (EP) .................................. 12171024

(51) Int. Cl.
*C12M 1/00* (2006.01)
*A01N 1/00* (2006.01)
(Continued)

(52) U.S. Cl.
CPC ......... *C12M 23/40* (2013.01); *A61L 27/3895* (2013.01); *C12M 23/00* (2013.01);
(Continued)

(58) Field of Classification Search
CPC ............ A61L 27/3847; A61L 27/3895; C12N 5/0062; C12N 5/0663; C12N 2533/14; C12M 25/14; C12M 29/04
See application file for complete search history.

(56) References Cited

U.S. PATENT DOCUMENTS

2008/0318315 A1* 12/2008 Martin ................ A61L 27/3847
435/377

FOREIGN PATENT DOCUMENTS

DK     WO 2011029450 A1 *  3/2011 ............ C12M 33/00

* cited by examiner

*Primary Examiner* — Michael Hobbs
(74) *Attorney, Agent, or Firm* — Hoffmann & Baron, LLP

(57) ABSTRACT

A bioreactor for preferably three-dimensional cell culturing comprises a scaffold chamber, a first tube, a second tube and a first valve with a scaffold adapter, a tube adapter and a medium adapter. The first valve has a housing with a longitudinal female portion ending in an opening and a longitudinal actuator being arranged through the opening of the female portion of the housing such that the actuator is arranged partially inside the housing and partially outside the housing, wherein the actuator of the first valve is axially moveable relative to the housing of the first valve between a first position in which the first valve is in the operation position and a second position in which the first valve is in the medium change position. By providing the actuators in the first valve which is applied by axial movements, operation of the bioreactor can be comparably simple and safe.

10 Claims, 7 Drawing Sheets

(51) Int. Cl.
*C12N 5/00* (2006.01)
*A61L 27/38* (2006.01)
*C12M 1/12* (2006.01)
C12N 5/0775 (2010.01)

(52) U.S. Cl.
CPC ............ C12M 25/14 (2013.01); C12M 29/00 (2013.01); C12N 5/0062 (2013.01); *A61L 27/3847* (2013.01); *C12N 5/0663* (2013.01); *C12N 2533/14* (2013.01)

BIOREACTOR AND RACK FOR MOUNTING BIOREACTORS

CROSS-REFERENCE TO RELATED APPLICATIONS

This application is the U.S. National Phase of International Patent Application No. PCT/EP2013/061514 filed on 4 Jun. 2013, which claims benefit of European Patent Application No. 12171024.8 filed on 6 Jun. 2012, the contents of which are incorporated herein by reference in their entireties.

TECHNICAL FIELD

The present invention relates to a bioreactor according to the preamble of independent claim 1 and to a mounting rack for mounting a plurality of bioreactors of this kind. Such bioreactors include a scaffold chamber, a first tube, a second tube and a first valve with a scaffold adapter, a tube adapter and a medium adapter, wherein the tube adapter of the first valve is connected to the first tube and the scaffold adapter of the first valve is connected to the scaffold chamber; the first valve is arrangeable in an operation position in which the scaffold adapter of the first valve is in fluid connection with the tube adapter of the first valve and the medium adapter of the first valve is fluid sealed to the tube adapter of the first valve; and the first valve is arrangeable in a medium change position in which the medium adapter of the first valve is in fluid connection with the tube adapter of the first valve and the scaffold adapter of the first valve is fluid sealed to the tube adapter of the first valve, can be used for preferably three-dimensional cell culturing, particularly tissue or tissue-like cell culturing such as bone tissue cell culturing.

BACKGROUND ART

In recent years, scientific evidence proving the inadequacy of monolayer cell cultures have triggered the development of techniques that allow culturing of cells in a three-dimensional (3D) environment. These techniques include the use of suitable porous biomaterials, i.e. scaffolds, that can be seeded with cells but can also include cell clusters, tissue or tissue like structures, biopsies and similar.

As a consequence, tools have been made available to respond to specific needs inherent to these techniques. Among these tools, bioreactors provide a controlled chemophysical environment suitable for the culturing of cells in 3D. In particular, perfusion bioreactors have proven to be effective in overcoming typical limitations of static cultures. Such limitations include lack of a uniform cell seeding through the scaffold, limited mass transport, i.e. nutrient delivery and waste removal, particularly in a central part of the scaffold.

For example, in the article "Uniform tissues engineered by seeding and culturing cells in 3D scaffolds under perfusion at defined oxygen tension" of Wendt D. et al. from the Departments of Surgery and of Research of the University Hospital Basel, Switzerland, published in Biorheology, 43, 481-488, 2006, a bioreactor for 3D cell culturing is shown. This bioreactor comprises a first tube and a second tube each being connected to a scaffold chamber via a three way valve. The first tube is made of Teflon and provided with a cell suspension. The second tube comprises a portion made of Teflon and a flexible portion. The first tube and the flexible portion of the second tube are connected to a pump allowing to circulate the cell suspension through the scaffold chamber in which a porous scaffold is arranged. The three way valves are additionally connected to the pump and a medium storage. The valves are further arranged to be in medium change position in which the first and second tubes are in fluid connection with the medium storage and an operation position in which the first and second tubes are connected to the scaffold chamber.

However, such bioreactors are usually comparably cumbersome to set up and to operate such that mistakes impairing cell culturing can occur. For example, when setting up such a bioreactor numerous components of various vendors have to be manually assembled wherein these components frequently do not properly fit together. Further, such bioreactors are typically made of comparably expensive recyclable components that are used for multiple cycles which bears the risk of accumulation of undesired substances. Still further, the three way valves used within such bioreactors usually have to be operated by rotating an actuator in various proper rotational positions. Operation of these three way valves often is confusing and can easily induce mistakes when being handled particularly by inexperienced users.

Therefore, there is a need for a bioreactor and system allowing for a convenient operation and handling within cell culturing.

SUMMARY

According to the invention this need is settled by a bioreactor as it is defined by the features of independent claim 1, and by a rack as it is defined herein below. Preferred embodiments are subject of the dependent claims.

In particular, the gist of the invention is: A bioreactor for preferably three-dimensional cell culturing includes a scaffold chamber, a first tube, a second tube and a first valve with a scaffold adapter, a tube adapter and a medium adapter. The tube adapter of the first valve is connected to the first tube and the scaffold adapter of the first valve is connected to the scaffold chamber. The first valve is arrangeable in an operation position in which the scaffold adapter of the first valve is in fluid connection with the tube adapter of the first valve and the medium adapter of the first valve is fluid sealed to the tube adapter of the first valve. The first valve further is arrangeable in a medium change position in which the medium adapter of the first valve is in fluid connection with the tube adapter of the first valve and the scaffold adapter of the first valve is fluid sealed to the tube adapter of the first valve. Thereby, the first valve has a housing with a longitudinal female portion ending in an opening and a longitudinal actuator being arranged through the opening of the female portion of the housing such that the actuator is arranged partially inside the housing and partially outside the housing, wherein the actuator of the first valve is axially moveable relative to the housing of the first valve between a first position in which the first valve is in the operation position and a second position in which the first valve is in the medium change position.

The bioreactor can particularly be a perfusion bioreactor suitable for bone or cartilage tissue culturing. The term "adapter" as used in the context of the invention relates to any possible connection of two units or of two portions of one single unit. In particular, an adapter can be a connector of a first unit allowing for mounting and dismounting a corresponding connector of a second unit. Or, an adapter can also be the connecting portion of a single unit such as a tubular portion connecting two portions of one unit or a passage connecting two portions of one unit. Particularly, the scaffold adapter of the first valve can be fixedly mounted to the scaffold chamber, wherein the scaffold adapter and at least a part of the scaffold chamber can be made as one piece. The first and the second tube can be made of silicone such that they are slightly permeable, particularly for oxygen and/or for carbon dioxide. The first valve can be made of polycarbonate and/or acrylonitrile butadiene styrene (ABS), e.g. such that it is not autoclavable in order to avoid reuse, if desired. The actuator can be essentially circular cylindrical or essentially polygonal cylindrical. The term "axially" with regard to the actuator relates to a direction along a longitudinal axis of the actuator.

By providing the actuator in the first valve which is applied by axial movements, operation of the bioreactor can be comparably simple and safe. In particular, such arrangement allows for a comparably easy identification of the position of the first valve, i.e., e.g., if the valve is in the medium change position or in the operation position. Furthermore, it also allows for exactly adjusting the position of the actuator such that also positions in between the medium change position and the operation position can be conveniently identified and applied, if necessary.

Preferably, the bioreactor further includes a second valve with a scaffold adapter, a tube adapter and a medium adapter, wherein the tube adapter of the second valve is connected to the second tube and the scaffold adapter of the second valve is connected to the scaffold chamber; the second valve is arrangeable in an operation position in which the scaffold adapter of the second valve is in fluid connection with the tube adapter of the second valve and the medium adapter of the second valve is fluid sealed to the tube adapter of the second valve; the second valve is arrangeable in a medium change position in which the medium adapter of the second valve is in fluid connection with the tube adapter of the second valve and the scaffold adapter of the second valve is fluid sealed to the tube adapter of the second valve; the second valve has a housing with a longitudinal female portion ending in an opening and a longitudinal actuator being arranged through the opening of the female portion of the housing such that the actuator is arranged partially inside the housing and partially outside the housing; and the actuator of the second valve is axially moveable relative to the housing of the second valve between a first position in which the second valve is in the operation position and a second position in which the second valve is in the medium change position.

As the first valve mentioned above, also the second valve can be made of polycarbonate and/or ABS and its actuator can be essentially circular cylindrical or essentially polygonal cylindrical. Providing the second valve within the bioreactor allows for a particular efficient operation. Thereby, the second valve including the actuator being applicable by axial movements in correspondence with the first valve allows for operating the bioreactor in a comparably simple and safe manner. In particular, such arrangement also allows for a comparably easy identification of the position of the second valve, i.e., e.g., if the valve is in the medium change position or in the operation position. Furthermore, it also allows for exactly adjusting the position of the actuator such that also positions in between the medium change position and the operation position can be conveniently identified and applied, if necessary.

Thereby, each of the first valve and the second valve preferably is arranged such that the tube adapter is essentially opposed to the scaffold adapter wherein the actuator has a through bore connecting the tube adaptor and the scaffold adaptor in the operation position of the respective valve. In this context, the term "respective valve" with regard to the actuator relates to the valve of which the actuator forms a part. For example, the first valve is the respective valve of the actuator of the first valve. As mentioned above, in the operation position of the respective valve the actuator is in the first position. The through bore can have a circular profile and can be a straight through bore. Such an arrangement of the valves can allow for a comparably easy implementation of the bioreactor.

The actuator of each of the first valve and the second valve preferably has an inner duct connecting the medium adaptor and the tube adaptor in the medium change position of the respective valve. As mentioned above, in the medium change position of the respective valve the actuator is in the second position. Thereby, the inner duct of the actuator of each of the first valve and the second valve preferably has an essentially axial portion and an essentially radial portion. Such an arrangement of the valves can allow for a comparably easy and precisely operatable implementation of the bioreactor.

Preferably, the actuator of each of the first valve and the second valve has a flange portion. The flange portion can particularly be arranged in a distal end region of the corresponding actuator. It can also radially project above the rest of the actuator. Such a flange portion allows for an efficient operation of the valves. For example, a user of the bioreactor can conveniently manually move the actuators of the first and second valves via the respective flange portion.

Preferably, the housing of each of the first valve and the second valve has a guidance interacting with the actuator such that the actuator is solely axially moveable within a predefined range. Like this, the risk of faulty operation of the valves can be reduced. Also the valves can be provided in a comparable stable arrangement and a stroke of the actuator can be defined. Thereby, the guidance preferably comprises a groove and the actuator an arm wherein the arm of the actuator engages the groove of the housing of the respective valve. Beyond others, such a groove allows for example determining the stroke of the actuator via its length. In order to provide sufficient stability, the housing can particularly comprise two grooves and the actuator to corresponding arms.

Preferably, the scaffold chamber includes a casing wherein the casing of the scaffold chamber has a first part with a first bayonet mount structure and a second part with a second bayonet mount structure, wherein the casing is arrangeable in an open position in which the first part and the second part are disassemblable and in a closed position in which the first bayonet mount structure of the first part and the second bayonet mount structure of the second part are engaging. Such a casing which can be opened allows for conveniently accessing a scaffold in the scaffold chamber.

Thereby, the scaffold chamber preferably includes a scaffold holder wherein the scaffold holder is removable from the casing in the open position of the casing and the scaffold holder is enclosable inside the casing in the closed position of the casing. The scaffold holder can have an essentially cylindrical shape with an essentially cylindrical opening axially extending through the scaffold holder. The opening can be narrowed into the direction of one of the axial ends of the scaffold holder. This can, e.g., be provided by a bottom or top plate having a through bore of a smaller dimension than the opening of the scaffold holder. In particular, the scaffold holder can be essentially cup shaped with a through bore at its closed end for allowing accessing a scaffold being arranged inside the scaffold holder. Thereby, the scaffold can be positioned inside the scaffold holder by arranging it in the opening of the scaffold holder. At its outer surface, the scaffold holder can be provided with one or more recesses circumferentially extending around the scaffold holder. Each of the one or more recesses can be arranged for accommodating a sealing ring such that the scaffold holder can be arranged in the casing in a sealed manner. The outer surface of the scaffold holder can further be provided with gripping surfaces which allow an efficient handling of the scaffold holder. The scaffold holder allows for holding the scaffold in a preferred manner such that a convenient and efficient handling is possible as well as an efficient operation of the bioreactor.

The scaffold chamber further preferably includes blocking adapters being arrangeable in the scaffold holder to embed the scaffold. Advantageously there are two blocking adapter which can be made of silicone. The blocking adapters can be essentially ring shaped wherein the interior opening can be provided with a step for accommodating the scaffold. The blocking adapters can particularly be shaped to be tightly arranged in a scaffold holder as mentioned above. One of the axial end sides of each of the blocking adapters can be colored for allowing convenient correct insertion into the scaffold holder. Blocking adapters as described herein allow for a safe and soft fixation of the scaffold in a predefined position within the bioreactor.

Preferably, the medium adapter of the actuator of each of the first valve and the second valve comprises a male locking thread. The male thread can be a luer-lock thread and particularly a double luer-lock thread. Such a male locking thread allows for conveniently and safely mounting a tubular medium structure to the bioreactor.

Another aspect of the present disclosure relates to a rack for mounting a plurality of bioreactors as described above. The rack includes a frame with a plurality of mounting structures wherein each mounting structure comprises a tube holder arranged to hold a first tube of one of the plurality of bioreactors and a second tube of the one of the plurality of bioreactors, and a guiding arch arranged to turn the first tube or the second tube of the one of the plurality of bioreactors. The tube holder of each mounting structure can be arranged to hold the first tube of one of the plurality of bioreactors at an end region opposite to a scaffold chamber of the one of the plurality of bioreactors and the second tube of the one of the plurality of bioreactors at an end region opposite to the scaffold chamber of the one of the plurality of bioreactors. The guiding arch allows to arrange the first and second tubes such that their end regions opposite to the scaffold chamber are heading into the direction of the corresponding tube holder. In particular, the guiding arch can be arranged to turn the first tube or the second tube about 180° such that it is arranged to U-turn the first tube or the second tube.

The rack allows for correct positioning of the bioreactors and particularly of the flexible parts thereof such that their proper functioning can be achieved. It can provide stability during operation and in an incubator for cell culturing. It also can provide comparably good visibility and comparably easy access all bioreactors mounted in the rack. It further allows for an efficient organisation of the bioreactors and particularly of tubes going from a pump to the single bioreactors. It also makes a compact and safe arrangement and comparable easy transportation possible. In summary, with such a rack a particularly comfortable and efficient correct handling of plural bioreactors requiring comparably little space can be provided.

Preferably, each of the tube holders of the plurality of mounting structures includes a plate with two clamping portions arranged to clamp the first tube and the second tube of one of the plurality of bioreactors. Such clamping portions allow for a comparably simple implementation of the tube holders. For example, the tube holders can be shaped as two essentially rectangular plates with a U-shaped recess at each longitudinal end as the clamping portions.

Preferably, the rack includes a base wherein the frame is turnably mounted on the base such that the frame is turnable about an essentially vertical axis when the rack is positioned on the base. Such a turnable rack allows for conveniently accessing each of the bioreactors mounted in the rack.

Preferably, the rack includes an operating handle which can allow for a convenient and efficient handling of the rack. Preferably, each of the plurality of mounting structures or a group mounting structures of the plurality of mounting structures is arranged as a removable unit. Such removable units can further improve handling of the bioreactors within the rack.

These and other aspects of the invention will be apparent from and elucidated with reference to the embodiment(s) described hereinafter.

BRIEF DESCRIPTION OF THE DRAWINGS

The bioreactor and the rack according to the invention are described in more detail herein below by way of exemplary embodiments and with reference to the attached drawings, in which.

DETAILED DESCRIPTION

In the following description certain terms are used for reasons of convenience and are not to be interpreted as limiting. The terms "right", "left", "horizontal", "vertical", "up", "down", "under" and "above" refer to directions in the figures. The terminology includes the explicitly mentioned terms as well as their derivations and terms with a similar meaning. Furthermore, if, in order to clarify the drawings, a figure contains reference signs which are not explained in the directly associated part of the description, then it is referred to previous description sections.

Figure 1:
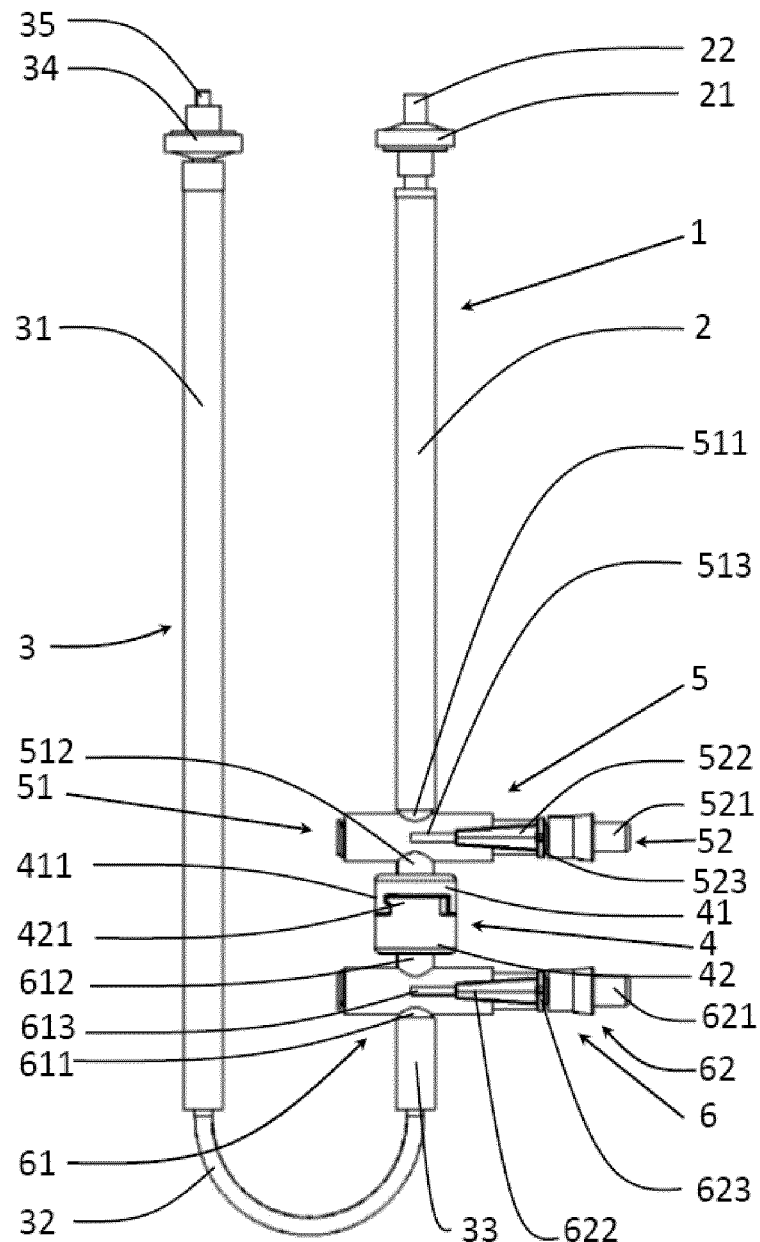
FIG. 1 shows a side view of an embodiment of a bioreactor according to the invention.
Figure 2:
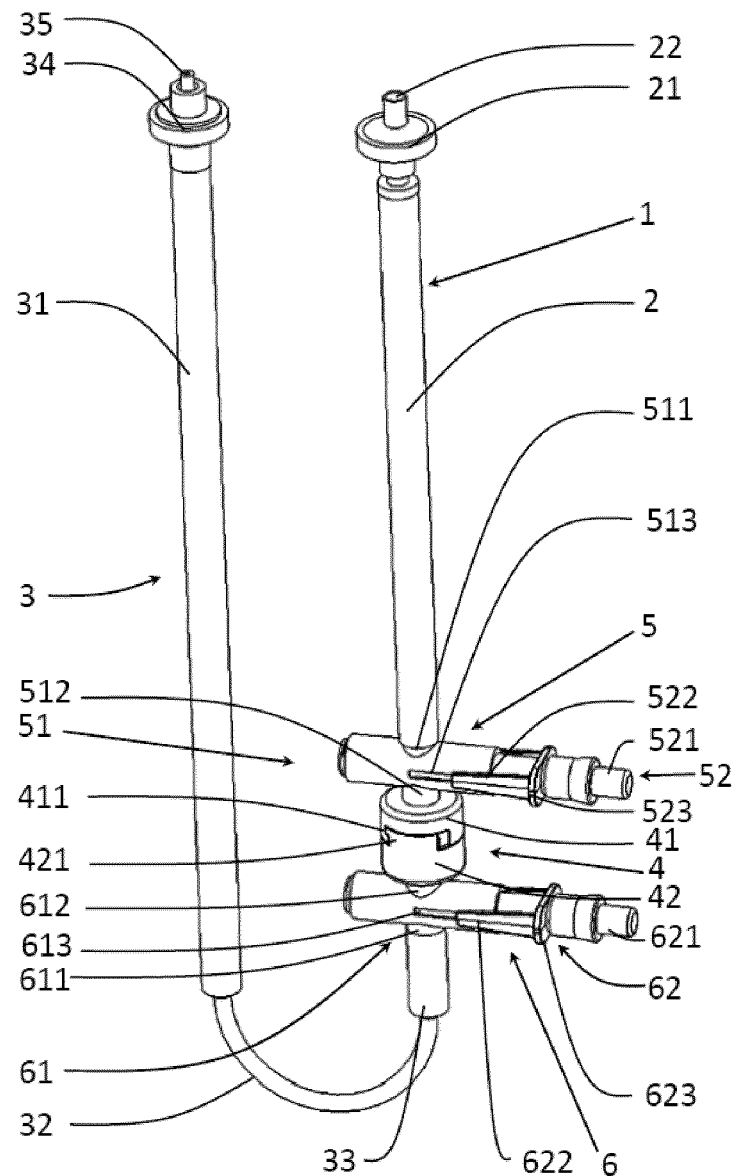
FIG. 2 shows perspective view of the bioreactor of FIG. 1.

In FIG. 1 and FIG. 2 an embodiment of a bioreactor 1 according to the invention includes a first tube 2, a second tube 3, a scaffold chamber 4, a first valve 5 and a second valve 6 is shown. The first tube 2 which is shown in FIG. 1 in an essentially vertical position is made of silicone being gas permeable particular for oxygen and carbon dioxide. On the top longitudinal or axial end of the first tube 2 a 0.2 µm first filter 21 is mounted by means of a luer-lock barbed connector for preventing exchange of microorganisms and particles into and out of the first tube 2. The first filter 21 has a first pump adapter 22 for connecting a pump. On the bottom longitudinal or axial end the first tube 2 is connected to a tube adapter 511 of a housing 51 of the first valve 5.

The first valve 5 includes an actuator 52 with an essentially cylindrical main body which in FIG. 1 is shown horizontally extending into the housing 51. At the one longitudinal end of the actuator 52 being arranged outside the housing, i.e. on the right hand end of the actuator 52 in FIG. 1, the actuator 52 has a medium adapter 521. Between the medium adapter 521 and the housing 51, the actuator 52 further comprises a flange portion 523 to which two arms 522 are arranged extending parallel to the main body of the actuator 52. As can be best seen in FIG. 2 the flange portion 523 of the actuator 52 has an essentially rectangular shape wherein it is horizontally arranged and wherein the arms 522 extend from the longitudinal ends thereof. The arms 522 of the actuator 52 extend into respective guidances 513 being arranged as horizontal slits in the housing 51. The arms 522 and guidances 513 allow for a stable movement of the actuator 52, for preventing a rotational movement of the actuator 52 around its longitudinal axis and for determining a stroke of the actuator via a length of the guidances 513.

Opposite to the tube adapter 511, i.e. in a downward direction, the housing 51 passes over into a scaffold adapter 512 being unitary built with an upper first part 41 of a casing of the scaffold chamber 4. The first part 41 of the casing of the scaffold chamber 4 includes a bayonet mount structure 411 which engages into a corresponding bayonet mount structure 421 of a second part 42 of the casing of the scaffold chamber 4. Thereby, the casing of the scaffold chamber 4 is in a closed position and the bayonet mount structures 411, 421 together provide a safety closing mechanism of the scaffold chamber 4. The second part 42 is unitary built with a scaffold adapter 612 of a housing 61 of the second valve 6. The second valve 6 is identical to the first valve 5 wherein compared to the first valve 5 it is arranged upside down such that the scaffold adaptor 612 of its housing 61 extends upwardly and a tube adaptor 611 of its housing 61 extends downwardly. Guidances 613 of the housing 61 and an actuator 62 with a medium adapter 621, a flange portion 623 and two arms 622 are arranged corresponding to the respective parts of the first valve 5. The bayonet mount structure 411 of the first part 41 and the bayonet mount structure 421 of the second part 42 are arranged such that the actuator 52 of the first valve 5 and the actuator 62 of the second valve 6 extend in parallel when the bayonet mount structure 411 of the first part 41 engages the bayonet mount structure 421 of the second part 42.

The tube adapter 611 of the housing 61 of the second valve 6 is connected to a second wide portion 33 of the second tube 3 which in FIG. 1 extends vertically. The second wide portion 33 of the second tube 3 is glued to a narrow portion 32 of the second tube 3 which describes a U turn. The gluing between the second wide portion 33 of the second tube 3 and the narrow portion 32 of the second tube 3 generates a conical shape that improves the fluidodynamic of the system and reduces cell settling on essentially horizontal surfaces. Also, the reduced diameter of the narrow portion 32 of the tube 3 is intended to increase flow speed in use such that cell settling in an essentially horizontal section of the second tube 3 can be reduced or even prevented. The end of the narrow portion 32 of the second tube 3 is again glued to a first wide portion 31 of the second tube 3 which in FIG. 1 extends vertically. Similar as mentioned before, the gluing between the end of the narrow portion 32 of the second tube 3 and the first wide portion 31 of the second tube 3 generates a conical shape that improves the fluidodynamic of the system and reduces cell settling on essentially horizontal surfaces. As the first tube 2, the second tube 3 is also made of silicone being gas permeable particular for oxygen and carbon dioxide.

On the top longitudinal or axial end of the first wide portion 31 of the second tube 3 a 0.2 μm second filter 34 is mounted by means of a luer-lock barbed connector for preventing exchange of microorganisms and particles into and out of the second tube 3. The second filter 34 has a second pump adapter 35 for connecting a pump. The first pump adapter 22 of the first filter 21 and the second pump adapter 35 of the second filter 34 differ in shape in order to make sure that the correct side of the pump is connected to corresponding first tube 2 or second tube 3.

Figure 3:
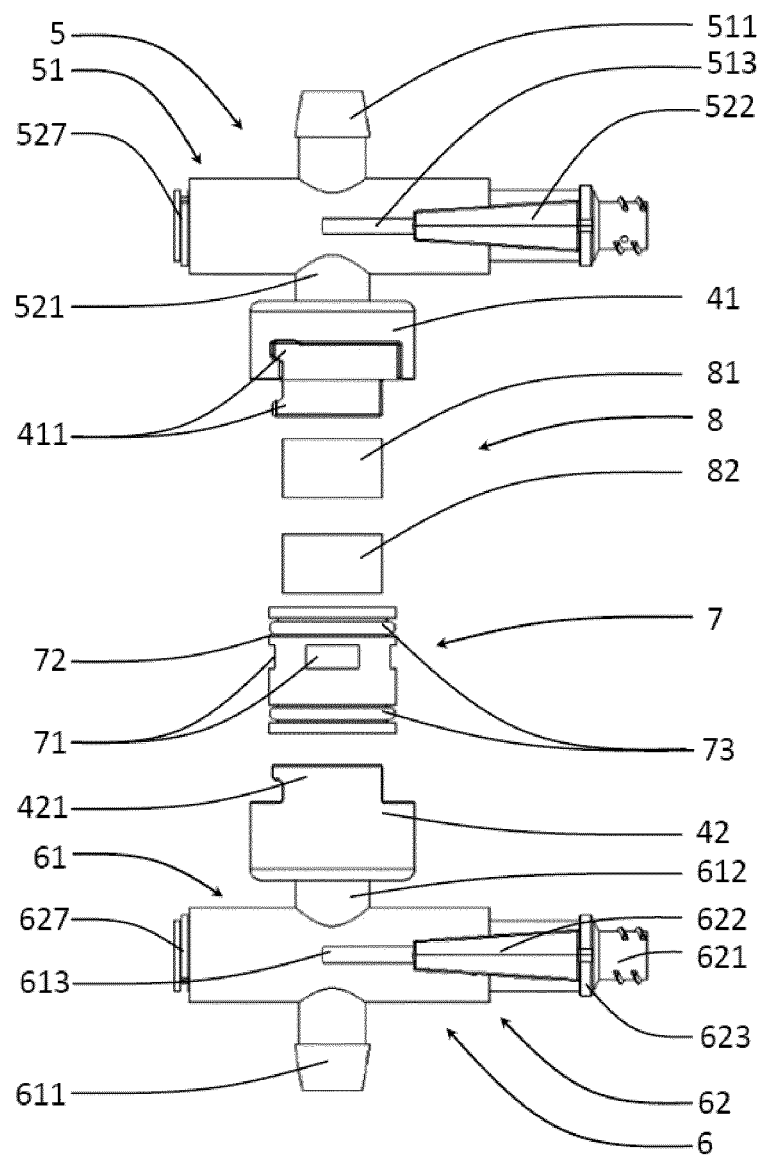
FIG. 3 shows an exploded side view of the valves, the scaffold chamber and parts inside the scaffold chamber of the bioreactor of FIG. 1.
Figure 4:
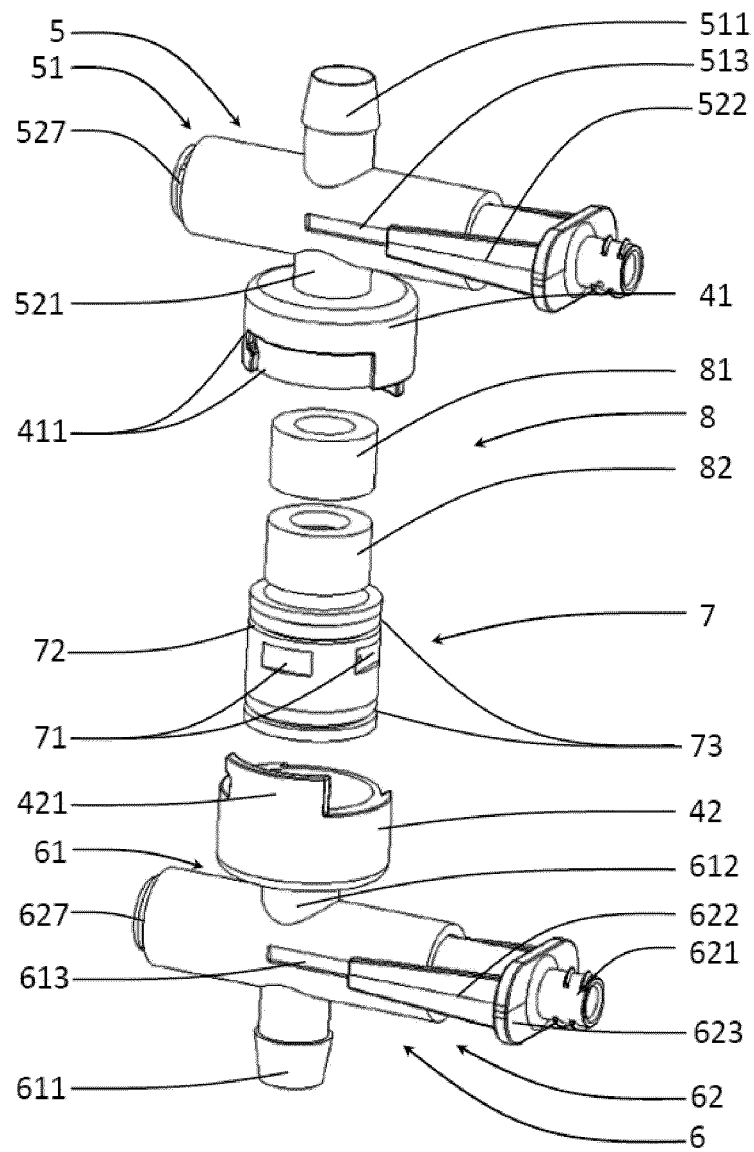
FIG. 4 shows an exploded perspective view of the valves, the scaffold chamber and the parts inside the scaffold chamber of the bioreactor of FIG. 1.

In FIG. 3 and FIG. 4 an exploded view of the scaffold chamber 4 of the bioreactor 1 is shown. In fact, FIG. 3 and FIG. 4 show the scaffold chamber 4 in a disassembled or open position in which the bayonet mount structure 411 of the first part 41 of the casing is disengaged from the bayonet mount structure 421 of the second part 42 of the casing. Thereby, a scaffold holder 7 and blocking adapters 8 are unloaded from the casing of the scaffold chamber 4. The blocking adapters 8 which both are made of silicone comprise a top first blocking adapter 81 and a bottom second blocking adapter 82 which both are made of silicone. In order that the blocking adapters 8 can be conveniently mounted in a correct manner, the first blocking adapter 81 is colored on its top side and the second blocking adapter is colored on its bottom side.

The scaffold holder 7 is essentially cylindrical and cup shaped. At its outer surface, the scaffold holder is provided with planar gripping surfaces 71 allowing for conveniently handling the scaffold holder 7. Near its top and bottom end recesses 72 are circumferentially arranged about the outer surface of the scaffold holder 7. In each of the recesses 72 a sealing O-ring 73 is arranged allowing for sealing a space between the scaffold holder 7 and the scaffold chamber 4 when the scaffold holder 7 is arranged inside the scaffold chamber 4 such that the scaffold holder 7 is held in the scaffold chamber 4 by friction forces between the sealing rings 73 and the scaffold chamber 4.

Figure 5:
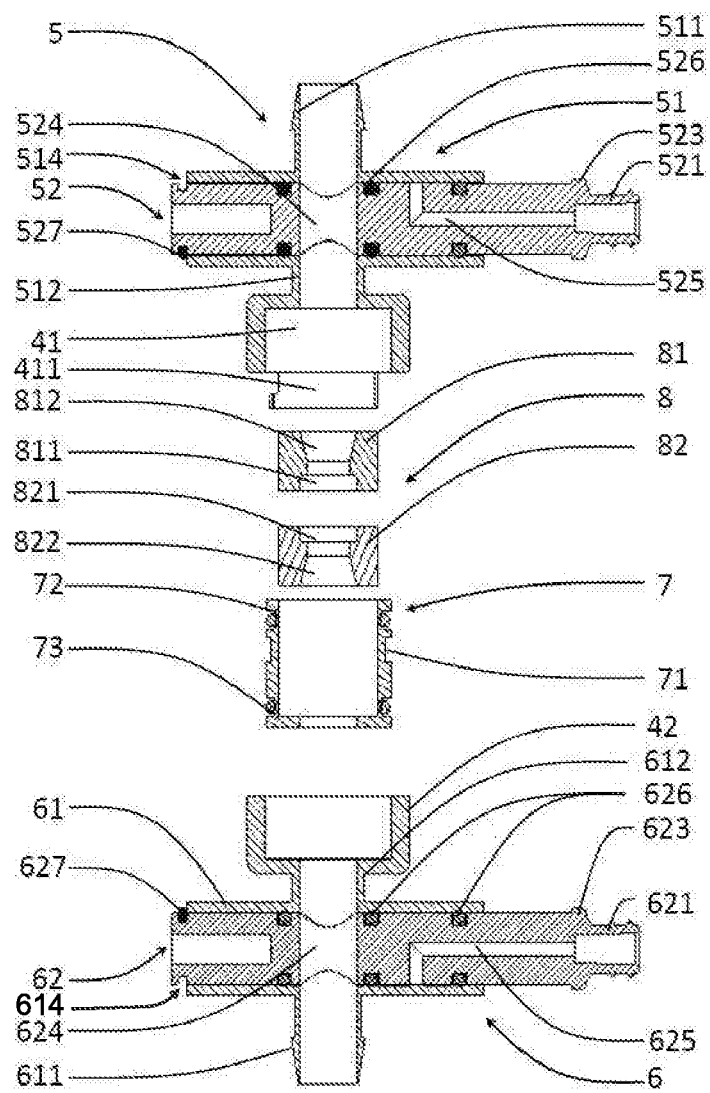
FIG. 5 shows an exploded cross-sectional side view of the valves in a operation position, the scaffold chamber and the parts inside the scaffold chamber of the bioreactor of FIG. 1.

In FIG. 5 cross-sections of the first valve 5, the scaffold chamber 4, the blocking adapters 8, the scaffold holder 7 and the second valve 6 are shown. The housing 51 of the first valve 5 has an essentially cylindrical horizontal through hole as a female portion 514. The actuator 52 is extending through the female portion 514 of the housing 51 wherein on one side, the right hand side, the flange portion 523 of the actuator 52 is arranged outside the housing 51 and on the other side, the left hand side, the actuator 52 has a circumferential recess outside the housing 51 in which a stop cramp 527 is snapped in. By means of this stop cramp 527 it can be prevented that the actuator 52 is removed out of the female portion 514 of the housing 52 into the direction of the medium adapter 521, i.e. to the right. The actuator 52 has vertical though bore 524 which in the operation position shown in FIG. 5 connects the tube adapter 511 with the scaffold adapter 512. The actuator 52 further has a duct 525 extending from the medium adapter 521 in an axial or horizontal direction to a certain extent and then turning by 90° in an upward vertical direction. In the operation position of the first valve shown in FIG. 5, the medium adapter 521 is neither connected to the tube adapter 511 nor to the scaffold adapter 512. Adjacent to the through bore 524 and the vertical opening of the duct 525, the actuator 52 has circumferential recesses with sealing O-rings 526. These sealing rings 526 allow for preventing any substance or contaminating agent entering or exiting out of the female portion 514 of the housing 51 or biasing the through bore 524 with the duct 525.

The first blocking adapter 81 and the second blocking adapter 82 each have a vertical through hole 812, 822 and a scaffold receiver 811, 821. Even though other shapes are also possible, both blocking adapters 8 are identically formed wherein they are arranged upside down in relation to each other such that the scaffold receiver 811 of the first blocking adapter 81 is directed to and adjacent to the scaffold receiver 821 of the second blocking adapter 82. Thereby, the scaffold receiver 811 of the first blocking adapter 81 and the scaffold receiver 821 of the second blocking adapter 82 together form a chamber for accommodating a scaffold in a safe and fixed position. The blocking adapters 81, 82 allow a tight sealing between the scaffold and the blocking adapters 81, 82 themselves, so that medium can effectively run through the porous scaffold instead of tangentially. The blocking adapters 8 are dimensioned to be tightly arranged inside the cup-shaped scaffold holder 7 such that they are held by friction between the blocking adapters 8 and inner surfaces of the scaffold holder 7. The bottom side of the scaffold holder 7 has a through hole allowing medium passing top down through the scaffold and the through holes 812, 822 of the blocking adapters 8 to exit the scaffold holder 7.

As described above in connection with FIG. 1 and FIG. 2, the second valve 6 is identical to the first valve 5 wherein compared to the first valve 5 it is arranged upside down. In particular, as can be seen in FIG. 5, its housing also comprises a female portion 614 and its actuator 62 also comprises a circumferential recess with a stop cramp 627, a vertical through bore 624, a duct 625 having a horizontal and a vertical section as well as circumferential recesses with sealing O-rings 626.

Figure 6:
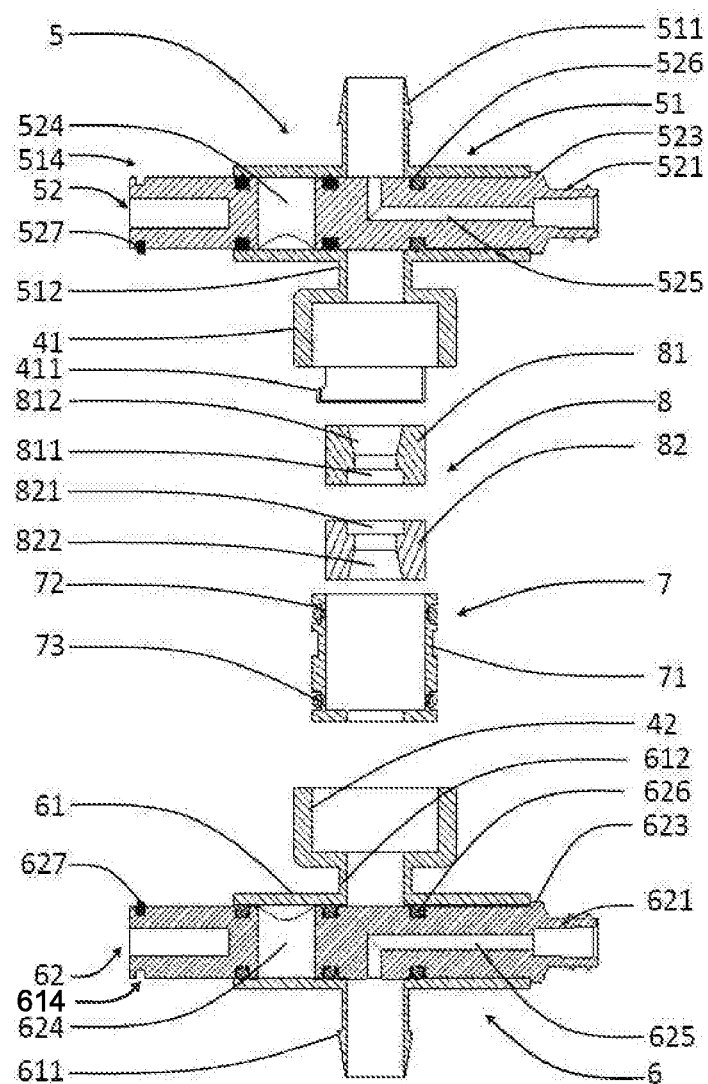
FIG. 6 shows an exploded cross-sectional side view of the valves in a medium change position, the scaffold chamber and the parts inside the scaffold chamber of the bioreactor of FIG. 1.

FIG. 6 shows the same component as FIG. 5 wherein contrary to the operation position of FIG. 5 the first valve 5 and the second valve 6 are shown in FIG. 6 in a medium change position. In this position, the actuators 52, 62 are horizontally moved into the direction of the stop cramps 527, 627, i.e. to the left, until the flange portions 523, 623 contact the respective housing 51, 62. Thereby, the ducts 525, 625 connect the tube adapters 511, 611 with the medium adapters 521, 621 of the respective valve 5, 6. Like this, medium can be added to or removed from the internal of the bioreactor 1 via the medium adapters 521, 621. For example, the medium adapter 521, 621 can be connected to a syringe which provides medium into the bioreactor 1.

In use of the bioreactor 1, once the scaffold is loaded into the blocking adapters 8 inside the scaffold holder 7 and inside the closed scaffold chamber 4, a cell suspension as medium can be provided into the bioreactor through the medium adapter 521, 621 of one of the valves 5, 6. Then the medium is moved in alternated directions by means of a syringe pump (or peristaltic) connected to the first filter 21 and second filter 34 for the time the culture requires while the valves 5, 6 are in the operation position. During this movement, the medium perfuses the sample and cell eventually attach to it. When medium needs to be changed, the valves 5, 6 can be moved to the medium change position by sliding the actuators 52, 62, exhaust medium is removed, fresh medium is injected, the valves 5, 6 are moved to operation position and the culturing continues.

Figure 7:
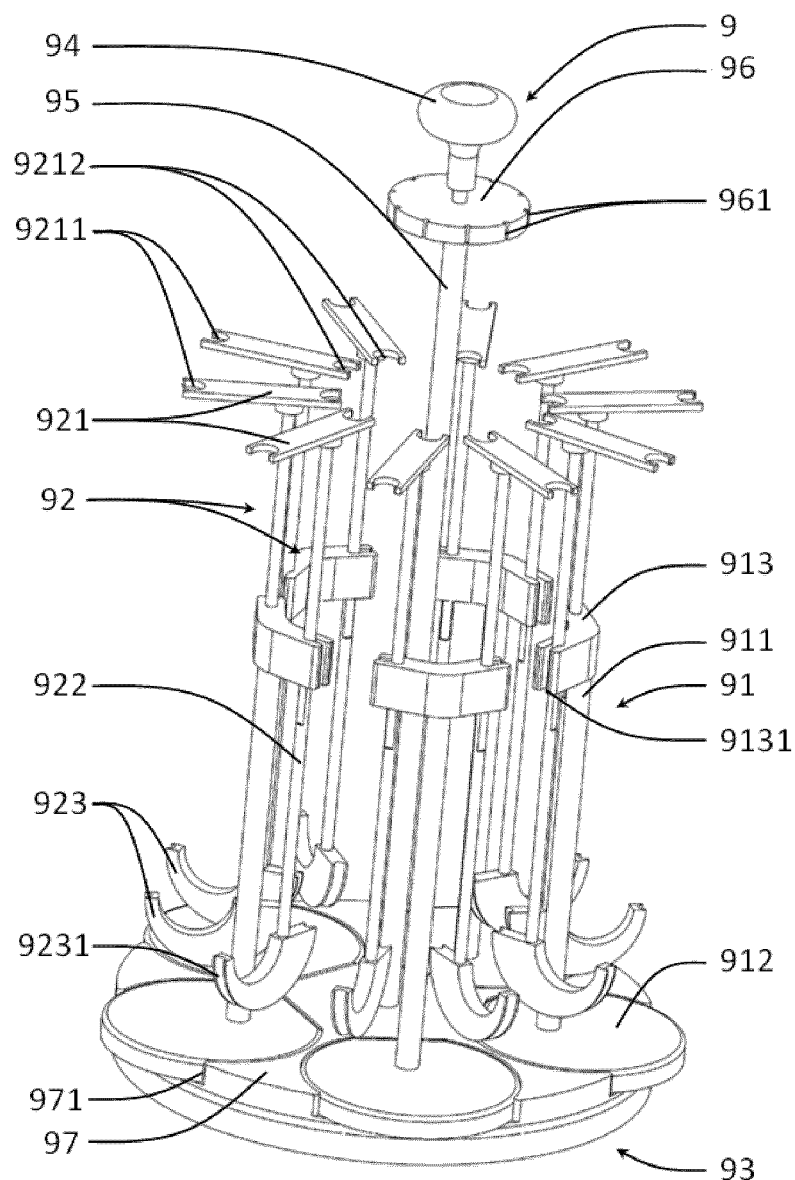
FIG. 7 shows a perspective view of an embodiment of a rack intended for mounting and handling a plurality of bioreactors according to the invention.

In FIG. 7 an embodiment of a rack 9 is shown which is intended for mounting and handling a plurality of bioreactors 1 as described above in connection with FIGS. 1 to 6. The rack 9 includes a frame having an essentially circle-disk-shaped frame base 97 with five evenly arranged, circle-segment-shaped recesses 971. The frame base 97 is turnably or rotatably mounted on top of a circle-disk-shaped rack base 93 as base of the rack 9. A linear handle rod 95 is centrally connected to the frame base 97 in a rotatably fixed manner. The handle rod 95 vertically extends from the frame base 97 in an upward direction when the rack base 93 is arranged on a horizontal surface such as on a table or the like. At its top end the handle rod 95 passes over into a handle grip 94 wherein the handle rod 95 and the handle grip 94 together form an operating handle of the rack 9. Near the handle grip 94 a circular disk 96 having plural tube slits 961 at its circumferential edge is mounted to the handle rod 95 wherein the handle rod 95 centrally traverses the circular disk 96.

In each of the recesses 971 of the frame base 97 a circle-disk-shaped unit base 912 of a removable unit 91 is arranged. From a top surface of the unit base 912 of each removable unit 91 a unit rod 911 vertically extends in an upward direction passing over into a crosspiece 913. Thereby, the unit rod 911 is connected to the unit base 912 at an eccentric position thereof. Each of the crosspieces 913 is slightly bent around the handle rod 95 as a central axis of the rack 9 wherein at its horizontal edges clamping slits 9131 are arranged.

In each of the clamping slits 9131 of the crosspieces 913 of the units 91 a connection rod 922 of a mounting structure 92 is clamped such that the connection rods 92 extend in an essentially vertical direction. At its bottom end each of the connection rods 922 passes over into a guiding arc 923 having a peripheral groove 9231. On the top end of each of the connection rods 922 an essentially horizontal and essentially rectangular plate 921 is mounted as tube holder. Each of the plates 921 has a first clamping recess 9211 as clamping portion and a second clamping recess 9212 as clamping portion at each of its shorter side edges.

In use of the rack 9, bioreactors 1 as described with regard to FIGS. 1 to 6 can be arranged in the rack 9 as follows: The first tube 2 of the bioreactor 1 is clamped into the first clamping recess 9211 of the plate 921 of one the mounting structures 92. The narrow portion 32 of the second tube 3 of the bioreactor 1 is arranged into the groove 9231 of the guiding arc 923 of said mounting structure 92 and thereby turned by about 180°. The first wider portion 31 of the second tube 3 of the bioreactor is then clamped into the second clamping recess 9212 of the plate 921 of said mounting structure 92.

The connection rod 922 of the mounting structure 92 is then clamped into one of the slits 9131 of the crosspiece 913 of one of the removable units 91. Optionally, a further mounting structure 92 with a further bioreactor 1 can be clamped into the other one of the slits 9131 of the crosspiece 913 of said removable unit 91. The unit base 912 of the removable unit 91 is then positioned into one of the recesses 971 of the frame base 97 of the rack 9. External tubes such as, e.g., air delivery tubes being connected to the bioreactor 1 can be clamped into the tube slits 961 of the disk 96 of the rack 9.

The rack 9 allows for safely holding one to ten bioreactors 1 in a preferred upright position. Thereby, the valves 5, 6 of all bioreactors 1 mounted to the rack 9 are conveniently accessible from the outside of the rack 9. Further, each of the bioreactors 1 in the rack 9 can easily be selected and accessed by turning the frame base 97 with respect to the rack base 93, e.g. via the handle grip 94, up to a desired position. In order to avoid for example wrapping up air tubes, rotation of the frame base 97 can be limited, e.g., to less than 360°. By means of the removable units 91 the bioreactors 1 can conveniently be mounted to and dismounted from the rack 9 wherein it can be assured that the bioreactors 1 are in a correct position and a wrong insertion can be prevented. In summary, the rack 9 allows for a convenient and flexible handling of plural bioreactors 1 in an organized and structured manner.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the FIGS. 1-7 individually although they may not have been described in the afore or following description. Also, single alternatives of the embodiments described in the figures and the description and single alternatives of features thereof can be disclaimed from the subject matter of the invention or from disclosed subject matter. The disclosure includes subject matter consisting of the features defined in the claims or the exemplary embodiments as well as subject matter including the features.

Furthermore, in the claims the word "comprising" does not exclude other elements or steps, and the indefinite article "a" or "an" does not exclude a plurality. A single unit or step may fulfill the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Any reference signs in the claims should not be construed as limiting the scope.

The present disclosure comprises the following further embodiments of racks intended for mounting and handling a plurality of bioreactors according to the invention.

Embodiment 1 is a rack for mounting a plurality of bioreactors according to the invention, including
a frame with a plurality of mounting structures wherein each mounting structure includes a tube holder arranged to hold a first tube of one of the plurality of bioreactors and a second tube of the one of the plurality of bioreactors, and
a guiding arch arranged to turn the first tube or the second tube of the one of the plurality of bioreactors.

Embodiment 2 is a rack according to embodiment 1, wherein each of the tube holders of the plurality of mounting structures includes a plate with two clamping portions arranged to clamp the first tube and the second tube of one of the plurality of bioreactors.

Embodiment 3 is a rack according to embodiment 1 or 2, including a base wherein the frame is turnably mounted on the base such that the frame is turnable about an essentially vertical axis when the rack is positioned on the base.

Embodiment 4 is a rack according to any one of embodiments 1 to 3, including an operating handle.

Embodiment 5 is a rack according to any one of embodiments 1 to 4, wherein each of the plurality of mounting structures or a group mounting structures of the plurality of mounting structures is arranged as a removable unit.

The invention claimed is:

1. A bioreactor for three-dimensional cell culturing, comprising a scaffold chamber, a first tube, a second tube, and a first valve with a scaffold adapter, a tube adapter, and a medium adapter, wherein:
the scaffold chamber comprises a casing having a first part with a first bayonet mount structure and a second part with a second bayonet mount structure, the casing arrangeable in an open position in which the first part and the second part are disassemblable and in a closed position in which the first bayonet mount structure of the first part and the second bayonet mount structure of the second part are engaging;
the tube adapter of the first valve is connected to the first tube and the scaffold adapter of the first valve is connected to the scaffold chamber;
the first valve is arrangeable in an operation position in which the scaffold adapter of the first valve is in fluid connection with the tube adapter of the first valve and the medium adapter of the first valve is fluid sealed to the tube adapter of the first valve; and
the first valve is arrangeable in a medium change position in which the medium adapter of the first valve is in fluid connection with the tube adapter of the first valve and the scaffold adapter of the first valve is fluid sealed to the tube adapter of the first valve;
wherein the first valve has a housing with a longitudinal female portion ending in an opening and a longitudinal actuator being arranged through the opening of the female portion of the housing such that the actuator is arranged partially inside the housing and partially outside the housing, and
wherein the actuator of the first valve is axially moveable relative to the housing of the first valve between a first position in which the first valve is in the operation position and a second position in which the first valve is in the medium change position.

2. The bioreactor according to claim 1, comprising a second valve with a scaffold adapter, a tube adapter, and a medium adapter, wherein:
the tube adapter of the second valve is connected to the second tube and the scaffold adapter of the second valve is connected to the scaffold chamber;
the second valve is arrangeable in an operation position in which the scaffold adapter of the second valve is in fluid connection with the tube adapter of the second valve and the medium adapter of the second valve is fluid sealed to the tube adapter of the second valve; and
the second valve is arrangeable in a medium change position in which the medium adapter of the second valve is in fluid connection with the tube adapter of the second valve and the scaffold adapter of the second valve is fluid sealed to the tube adapter of the second valve;
wherein the second valve has a housing with a longitudinal female portion ending in an opening and a longitudinal actuator being arranged through the opening of the female portion of the housing such that the actuator is arranged partially inside the housing and partially outside the housing, and
the actuator of the second valve is axially moveable relative to the housing of the second valve between a first position in which the second valve is in the operation position and a second position in which the second valve is in the medium change position.

3. The bioreactor according to claim 2, wherein each of the first valve and the second valve is arranged such that the tube adapter is essentially opposed to the scaffold adapter, wherein the actuator has a through bore connecting the tube adaptor and the scaffold adaptor in the operation position of the respective valve.

4. The bioreactor according to claim 2, wherein the actuator of each of the first valve and the second valve has an inner duct connecting the medium adaptor and the tube adaptor in the medium change position of the respective valve.

5. The bioreactor according to claim 2, wherein the actuator of each of the first valve and the second valve has a flange portion.

6. The bioreactor according to claim 2, wherein the housing of each of the first valve and the second valve has a guidance interacting with the actuator such that the actuator is solely axially moveable within a predefined range.

7. The bioreactor according to claim 6, wherein the guidance comprises a groove and the actuator comprises an arm wherein the arm of the actuator engages the groove of the housing of the respective valve.

8. The bioreactor according to claim 1, wherein the scaffold chamber comprises a scaffold holder wherein the scaffold holder is removable from the casing in the open position of the casing and the scaffold holder is enclosable inside the casing in the closed position of the casing.

9. The bioreactor according to claim 8, wherein the scaffold chamber comprises blocking adapters being arrangeable in the scaffold holder to embed the scaffold.

10. The bioreactor according to claim 2, wherein the medium adapter of the actuator of each of the first valve and the second valve comprises a male locking thread.

* * * * *